United States Patent [19]

Hanson et al.

[11] Patent Number: 4,752,221
[45] Date of Patent: Jun. 21, 1988

[54] ORTHODONTIC BRACKET

[75] Inventors: Gustaf H. Hanson, Hamilton; William M. Gibbon, Fonthill, both of Canada

[73] Assignees: Augusta Developments, Inc., Hamilton; Ontario Research Foundation, Mississauga, both of Canada

[21] Appl. No.: 660,546

[22] Filed: Oct. 16, 1984

Related U.S. Application Data

[63] Continuation of Ser. No. 486,159, Apr. 18, 1983, abandoned, which is a continuation-in-part of Ser. No. 302,011, Sep. 15, 1981, abandoned.

[51] Int. Cl.$^4$ .............................................. A61C 7/00
[52] U.S. Cl. ...................................................... 433/9
[58] Field of Search ...................... 433/8, 9, 201, 173, 433/174, 175

[56] References Cited

U.S. PATENT DOCUMENTS

| 3,775,850 | 12/1973 | Northcutt | 433/9 |
| 4,101,984 | 7/1978 | MacGregor | 3/1.5 |
| 4,243,386 | 1/1981 | Kawaguchi | 433/9 |
| 4,351,069 | 9/1982 | Ballintyn et al. | 433/201 |

FOREIGN PATENT DOCUMENTS 407694 7/1982 Canada .................................. 433/9

Primary Examiner—Robert Peshock
Attorney, Agent, or Firm—Rogers & Scott

[57] ABSTRACT

An orthodontic bracket of the type intended for cementing directly to a previously etched surface of the tooth enamel has on the lingual face thereof that contacts the tooth enamel surface a thin porous layer of sintered metal powder which is arranged to have a porosity such that it has keying characteristics close to that of the etched enamel and thereby facilitates the cementing adhesion of the bracket to the tooth. A particularly suitable metal powder consists of particles of the same alloy as the bracket metal and of size in the range about 10 to about 150 micons (−100 mesh), preferably from about 10 to about 50 microns (−300 mesh) applied in a thickness of about 0.05 to 0.2 mm, by means of a sintering operation that fuses the particles to the lingual face and to one another. The porous layer preferably is pre-filled with a polymer material compatible with the bonding cement, such as the sealant employed with the cement, so as to protect the layer against mechanical damage caused by bending of the bracket by the orthodontist to conform the bracket surface more closely to the tooth surface to which it is to be applied.

21 Claims, 1 Drawing Sheet

ORTHODONTIC BRACKET

CROSS-REFERENCE TO RELATED APPLICATIONS

This application is a continuation of our prior application Ser. No. 486,159, filed Apr. 18, 1983, now abandoned, which is a continuation-in-part of our prior application Ser. No. 302,011, filed Sept. 15, 1981, now abandoned.

FIELD OF THE INVENTION

The present invention is concerned with improvements in or relating to orthodontic brackets and especially to such brackets of the type which in use are bonded to etched enamel surfaces of the teeth.

REVIEW OF THE PRIOR ART

In the early days of orthodontic practice orthodontic brackets were fastened to respective metal bands which were then placed around the teeth, but an increasing number of orthodontists are using systems in which the brackets are bonded by a cement directly to the teeth surfaces. In one such known direct bonding system the bracket lingual face to which the cement is applied is provided by a thin sheet of fine metal mesh supported by a thin metal foil welded to the bracket body. The tooth surface enamel is first etched to a depth of about 0.01 mm, so as to improve the mechanical bonding of the cement thereto, and a thin layer of unfilled cement is applied over the etched area. A relatively thick layer of filled cement is applied to the lingual face of the metal mesh and pressed firmly into the interstices thereof, so as to maximise the mechanical bonding; the bracket is then pressed firmly into place on the tooth until a small amount of excess cement squeezes from the edges.

The filling of the cement, usually with very finely ground silica, is necessary to provide it with adequate anti-abrasion resistance in the highly hostile environment of the human mouth, unfilled cement being eroded relatively quickly. The use of a surplus of cement is necessary since the tooth surface usually is not particularly smooth and the foil is too stiff to be able to deform enough to follow the tooth contours under the pressure which is applied in affixing the bracket to the tooth. It is important to ensure that there are no voids or crevices between the bracket and the tooth surfaces in which, oral fluids, food particles, bacteria, etc., can lodge, since these could promote the formation of decay and could in an extreme case result in a cavity or cavities. It is of course fundamental that there be an excellent bond via the cement between each tooth and the bracket of sufficient strength to withstand the relatively high forces that are applied by normal every-day activities, extending over a period of up to about three years, while permitting the cement bond to be broken relatively easily at the conclusion of the procedure.

The lingual face of each bracket that is applied to the etched tooth surface is pre-formed during manufacture to approximately the curvature of the particular tooth to which it is to be applied. With approximately half of the brackets this pre-formed curvature provides a satisfactory match of the cement-joined surfaces, but with the other half the orthodontist must make some manual adjustment of the curvature (e.g. by use of pliers) to achieve an acceptable match.

The use of the above-described fine metal mesh has proven to be relatively satisfactory, the interwoven wires providing a large number of re-entrant crevices and the like into which the bonding cement can penetrate to provide the desired mechanical keying. Studies of bracket failures show that predominantly (90% thereof) they result from breaking of the bond between the cement and the bracket, and any improvement in this bond that can be obtained is therefore highly desirable. The production of the brackets involves the secure fastening of the mesh to the foil, and of the foil to the bracket, without damaging any of the components, and any improvements in cost, speed of manufacture, scrap rate reduction, etc., that can be obtained is of course desirable.

There is moveover a constant endeavour to reduce the size of the brackets, not only from the point of view of patient comfort because of the reduced bulk and protrusion, but also to give the orthodontist greater flexibility in the positioning of the brackets on the teeth, so that the required tooth movements can be obtained more readily and without the need to move the location of the brackets on the teeth during the procedure. However, such miniaturization reduces the area available over which the cement is operative for bonding the bracket to the tooth. Any reduction in thickness of the bracket element that is interposed between the bracket body proper and the tooth surface is highly desirable, in order to reduce the overall thickness of the bracket and its protrusion from the tooth.

DEFINITION OF THE INVENTION

It is therefore an object of the invention to provide an orthodontic bracket having a new kind of lingual surface for facilitating the bonding of the bracket to a tooth.

In accordance with the present invention there is provided an orthodontic bracket comprising a bracket body having a lingual surface which is applied to an acid-etched surface of a tooth on which the bracket body is to be mounted and bonded by a bonding material, the said lingual surface having thereon so as to be interposed between the said lingual and acid-etched surfaces a thin sintered layer of metal powder of thickness about 0.05 to about 0.2 mm and of particle size about 10 to 150 microns, the sintered layer being porous to the bonding material and having relatively elongated, tortuous, irregular, random pores extending in random directions from the surface thereof which receive the bonding material so as to provide a three-dimensional interconnecting network of capillaries that will become filled with the bonding material, the surface of the layer thereby corresponding at least approximately to the etched tooth surface to facilitate the bonding of the bracket to the tooth surface.

Preferably the sintered layer is pre-filled with a polymer material compatible with the bonding material by which the bracket is fastened to a tooth to facilitate mechanical handling and mechanical deformation of the sintered layer by the Orthodontist to conform it with the tooth surface to which it is to be applied.

DESCRIPTION OF THE DRAWINGS

Particular preferred embodiments of the invention will now be described, by way of example, with reference to the accompanying diagrammatic drawings, wherein.

DESCRIPTION OF THE PREFERRED EMBODIMENTS

Figure 1:
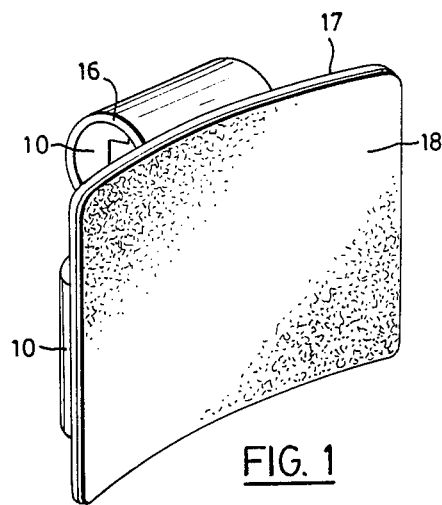
FIGS. 1 and 2 are respectively back and front perspective views of an orthodontic bracket of the invention.
Figure 2:
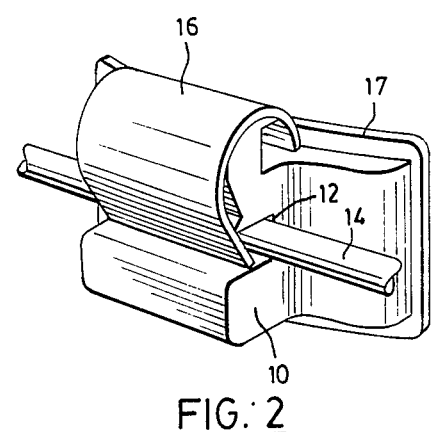

The bracket illustrated in FIGS. 1 and 2 is that described and claimed in U.S. Pat. No. 4,248,588 issued to G. Herbert Hanson. Briefly, the bracket consists of a body 10 of stainless steel having therein a mesial-distal extending slot 12 that receives an arch wire 14. The labial side of the slot is opened and closed as required, respectively for the insertion and retention of the arch wire, by respective movements of a generally U-shaped spring member 16 that embraces the bracket body and has an end that in the slot-closed position is urged by its inherent spring action to protrude into the slot 12 for engagement with the arch wire therein. The bracket has many other features that adapt it for its special task, but the exact structure of the bracket is not essential to a complete disclosure of the present invention, and further description thereof is believed to be unnecessary. One of the advantages of the Hanson bracket is the possibility of making it of very small dimensions and a current series has an occlusal-gingival height of 2.48 mm (0.098 in.), a mesial-distal width of 2.50 mm (0.1 in.) and a lingual-labial thickness of 1.52 mm (0.060 in.). The bracket body 10 has fastened to the lingual face thereof by accurate laser welding a thin piece 17 of a thin stainless steel metal foil of 0.15–0.2 mm (0.006–0.008 in.) thickness and about 3 mm by 4 mm (0.12 to 0.16 in.) dimensions with the longer edges extending mesially-distally.

Figure 4:
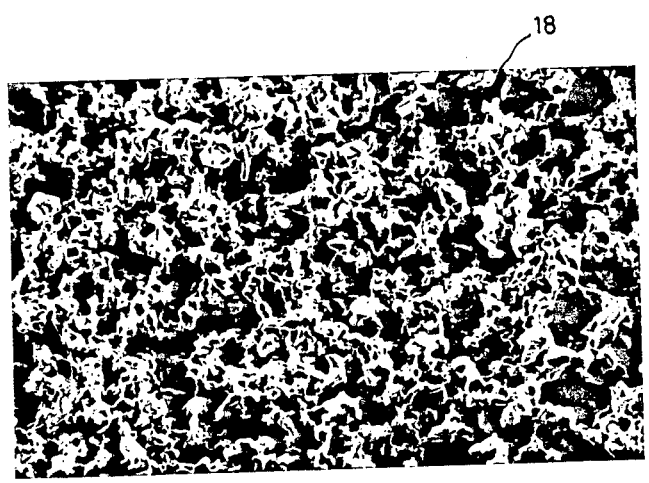
FIG. 4 is a photograph of a microscopic view of a small portion of the lingual surface of the brackets of FIGS. 1 and 2 to a magnification of 300 times, in order to show the nature of the surface obtained by the application of the invention.

Prior to its attachment to the bracket body this foil piece has applied to the lingual face thereof by a sintering operation one or more layers 18 of stainless steel metal particles in the size range of about 37 to 44 microns, the layer or layers 18 being of total thickness 0.13 mm (0.005 in.), so that the total thickness of the foil plus metal layer/s is about 0.33 mm (0.013 in.). The sintering operation is such that the particles are not only fused to the foil but they are fused to one another to form a resultant integral porous layer of irregular porosity, as is clearly seen from FIG. 4, or sandwich of porous layers, with excellent mechanical keying properties when a layer of the filled cement is applied to the lingual face of the bracket for its attachment to a tooth. With particles in this size range the resulting porous layer is found to have highly irregular random pores varying in size up to 100 microns across their major dimension. Moreover, these pores are found to be relatively elongated and tortuous, extending in random directions from the surface, their dimensions being such that they provide a three-dimensional interconnecting network of capillaries that will become filled with the bonding material. It is preferred to use the same stainless steel for the foil 16 and the metal powder layer 18 since ready adhesion by the sintering operation is thereby assured, or at least to use the same type of metal (e.g. stainless steel) but different metals can of course be used.

A relatively simple test of the adhesion capability of a particular cement/metal powder layer combination involves supporting a newly extracted tooth in some suitable manner, e.g. by burying it in a cement in a holder with the labial face exposed, cementing a bracket to the exposed tooth face and, after the cement has set, applying a progressively increasing tensile force to the bracket until it separates from the tooth. We suggest that a minimum acceptable figure for the applied tensile force is about 6 kg. Tests performed with brackets of the invention, employing the cement sold by 3M Corporation under the trade mark "CONCISE", showed that the brackets did not separate from the tooth when a force of about 6.7 kg was applied, failure occurring at the laser weld of the metal foil to the bracket body.

The following table shows the bond strength test values obtained from a series of such tests, tests 1–6 employing brackets with a foil-mesh base structure while tests 7–12 employ brackets with a powder-coated foil of the invention. In these tests failure occurred either at the cement-bracket interface or within the cement itself. These tests were carried out with twelve complete second premolar brackets as illustrated by FIGS. 1 and 2, of which half incorporated a foil-mesh bonding pad and the others, a powder-coated foil bonding pad of identical shape and peripheral dimensions. The surface area of each pad, calculated on the basis of gross dimensions, was 12.6 mm$^2$.

Two brackets (one of each type) were cemented directly opposite each other on a tooth, and a length of 0.43 mm dead soft wire was threaded through the auxiliary slot of each in turn and twisted to facilitate gripping by the jaws of an Instron tensile testing machine. With one wire in place, each tooth was mounted in turn in a special holder in the testing machine, and the force required to separate the bracket and the tooth was determined. A cross-head speed in the range 2.5 to 5.0 mm per minute was used. These tooth-bracket assemblies were exposed to air during the interval of approximately 3 hours which elapsed between cementing and testing.

TABLE 1

| Brackets Using Foil Mesh Base | | |
|---|---|---|
| Test No. | Load (kg) | Bond Strength (kg/mm$^2$) |
| 1 | 4.68 | 0.345 |
| 2 | 4.81 | 0.354 |
| 3 | 4.63 | 0.341 |
| 4 | 4.54 | 0.335 |
| 5 | 4.99 | 0.368 |
| 6 | 4.99 | 0.368 |
| Mean: | 4.77 | 0.352 |

TABLE 2

| Brackets Using Powder-Coated Foil Base | | |
|---|---|---|
| Test No. | Load (kg) | Bond Strength (kg/mm$^2$) |
| 7 | 7.72 | 0.569 |
| 8 | 8.94 | 0.659 |
| 9 | 8.17 | 0.602 |
| 10 | 9.53 | 0.702 |
| 11 | 9.99 | 0.736 |
| 12 | 9.53 | 0.702 |
| Mean: | 8.99 | 0.662 |

It will be seen that the mean bond strength with the powder coated foils is 0.662 kg/mm$^2$ while the mean value for foil mesh bases tested under the same conditions is only 0.352 kg/mm$^2$, so that a clear substantial improvement is obtained.

The mean bond strengths of both the foil mesh and the powder-coated foil do not appear to compare favourably with tensile bond strength as high as 1.83 kg/mm$^2$ reported with use of highly filled diacrylate cement and foil mesh. However, different testing methods and a different cement were used, and owing to time constraints the cement used in the test series described above was allowed to set for only 3 hours prior to testing. The manner in which the pull was applied to the brackets generates a rotational moment and a concentration of stresses at the nearest laser welds, to initiate a localized bond failure which can then spread as the dead soft foil is pulled away from the tooth. Although the specimens were subjected to pull tests, the actual stresses created at the various interfaces could have contained both shear and tensile components in varying proportions. The type of stress on any given area of an interface would have been dependent upon its orientation relative to the line of action of the test force.

Figure 3:
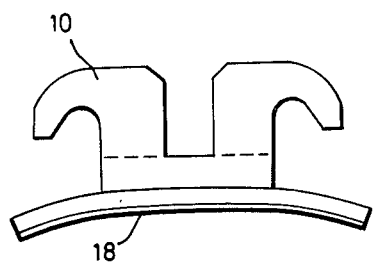
FIG. 3 is a top plan view of another orthodontic bracket embodying the invention.

The embodiment of FIG. 3 is a well-known bracket of the type which is attached to an arch wire (not shown) by means of one or more tie wires (also not shown). In this embodiment the metal powder layer 18 is applied directly to the lingual face of the body 10 instead of to a separate foil. When an intermediate foil is used this preferably will be of thickness from about 0.11 mm to 1.25 mm, (0.004 to 0.010 in.). The thickness of the metal powder layer preferably is from about 0.5 mm to 10.2 mm (0.002 to 0.008 in.), so that the thickness of the resultant sandwich is from about 0.15 mm to 0.45 mm (0.006 to 0.018 in.). The minimum satisfactory thickness of a prior art foil/metal mesh sandwich is about 0.2 mm (0.008 in.).

It is believed that the excellent bonding obtained with the brackets of the invention is due to the fact that the sintered metal porous layer or layers corresponds at least approximately in its keying characteristics to the etched enamel tooth surface, so that the cement employed is able to provide a satisfactory bond both to the tooth surface and the bracket surface. To this end the size of the metal powder particles should be within the range 10 to 150 microns, but preferably are within the range 30 to 50 microns. It is preferred that the particles be of size such that the difference between the smaller and the larger particles is not more than about 50 microns, this uniformity in size ensuring that they will not pack too densely, so as to leave a large number of the above-mentioned random elongated pores into which the cement can penetrate for mechanical keying thereto. It will be understood by those skilled in the art that when dealing with particles of this size there is no abrupt cut-off in size and although the difference between the statistically smaller and larger particles is 50 microns there will in fact be present a much wider range of sizes, but of numbers too small to be significant. It will also be appreciated that the range of particle size for a particular metal powder will be chosen predominantly to ensure a satisfactory bond of the cement to the layer 18; adequate bonding of the metal particles to one another will usually be less critical in such choice since the required particle-to-particle connection strength is more easily obtained by a sintering operation and, as indicated above, the majority of failures have previously occurred in the cement/foil interface and not the bracket/foil junction.

The particle size employed is readily determined by the size of mesh through which the powdered material will pass. Thus, a 100 mesh sieve will pass particles of size less than 149 microns but retain any larger, while a 300 mesh sieve will pass particles less than 50 micron size; the preferred material is that which will pass through the 300 mesh sieve.

In other embodiments it may be preferred to apply the metal powder layer 18 in more than one stage. For example, a first sub-layer can be applied directly to the foil or bracket lingual face which sub-layer is of smaller size particles and/or of a wide range to achieve denser packing; the layer 18 is completed by the application of one or more other sub-layers of particle size and distribution preferred to provide the desired mechanical characteristics for adequate keying of the cement thereto.

A very satisfactory procedure for fastening the particles of the metal powder layer to the remainder of the bracket, and to one another, is by sintering at about three quarters of the melting temperature. As a specific example, when the material of the foil 16 and the layer 18 is an austenitic stainless steel with a melting point of about 1480° C. (2700° F.) the sintering will be carried out at about 1100° C. to 1250° C. (2012° F. to 2282° F.) for about one half hour in a vacuum or hydrogen atmosphere.

As described above, in a typical orthodontic practice the orthodontist first etches the surfaces of the teeth to which brackets are applied and then applies a layer of unfilled or lightly-filled enamel sealant to the etched surfaces. A suitable sealant is that sold for example by Reliance Orthodontic Products of Itasca, Ill. as the sealant portion of its "Phase II orthodontic adhesive system", consisting of clear, so-called "A" and "B" liquids that are mixed just prior to application and sponged onto the etched tooth surface. The cement portion proper of this system is a paste-like material, also supplied as "A" and "B" components, consisting of the sealant liquids filled with very finely divided silica. The paste components are mixed and promptly employed in the manner described above.

We have found it preferable for the orthodontic brackets to have the porous layer thereof pre-filled with a polymer material, such as unfilled or lightly-filled sealant material that is compatible with the bonding cement, since this facilitates the handling of the brackets, and particularly the mechanical bending deformation by the orthodontist to match the shape of the cement receiving lingual surface to that of the tooth surface to which it is to be applied. As mentioned above, about one half of the brackets must be manipulated in this manner. It has been found that even if this bending manipulation is of such severity that cracks appear in the polymer these appear to be repaired by usual application of sealant by the orthodontist just prior to the application of the bracket to the teeth, so that the orthodontist is given much more freedom of operation in this regard. The unfilled sealant material is used since it is of course inherently compatible with the paste material of the system, but any other compatible material can be employed.

The porous layer is found to be inherently somewhat easily crushed by the type of mechanical handling and deformation required to conform the foil to the tooth shape. Visual inspection of such a crushed portion shows the surface to have a burnished, compacted appearance contrasting clearly with the characteristic porous appearance of the remainder of the surface, and the crushed portion no longer exhibits the required excellent keying characteristics it possessed prior to the handling and deformation. A bracket of the invention with the porous layer pre-filled as described is found to be capable of manipulation and deformation without this loss of keying characteristic, and is preferred by the orthodontist because of the ease of operation that it provides.

We claim:

1. An orthodontic bracket comprising a bracket body having a lingual surface which is applied to an acid-etched surface of a tooth on which the bracket body is to be mounted and bonded by a bonding material, the said lingual surface having thereon so as to be interposed between the said lingual and acid-etched surfaces a thin sintered layer of metal powder of thickness about 0.05 to about 0.2 mm and of particle size about 10 to about 150 microns, the sintered layer being porous to the bonding material and having relatively elongated, tortuous, irregular, random pores extending in random directions from the surface thereof which receives the bonding material so as to provide a three-dimensional interconnecting network of capillaries that will become filled with the bonding material, the surface of the layer thereby corresponding at least approximately to the etched tooth surface to facilitate the bonding of the bracket to the tooth surface.

2. An orthodontic bracket as claimed in claim 1, wherein the sintered layer is pre-filled with a polymer material compatible with the bonding material by which the bracket is fastened to a tooth to facilitate mechanical handling and mechanical deformation of the sintered layer to conform it with the tooth surface to which it is to be applied.

3. An orthodontic bracket as claimed in claim 2, wherein the sintered layer is pre-filled with the sealant component of the bonding material employed for fastening the bracket to a tooth.

4. An orthodontic bracket as claimed in claim 1, wherein the metal of the sintered layer is the same as that of the bracket lingual surface to which it is applied.

5. An orthodonitc bracket as claimed in claim 2, wherein the metal of the sintered layer is the same as that of the bracket lingual surface to which it is applied.

6. An orthodontic bracket as claimed in claim 1, wherein the said sintered layer of metal powder is carried by a separate thin metal foil constituting part of the bracket and fixed to the remainder of the bracket body.

7. An orthodontic bracket as claimed in claim 6, wherein the said metal foil is of thickness about 0.1 to 0.25 mm, and the total thickness of the metal foil and the sintered layer is about 0.15 to 0.45 mm.

8. An orthodontic bracket as claimed in claim 1, wherein the metal powder is of particle size about 30 to 50 microns.

9. An orthodontic bracket as claimed in claim 1, wherein the particles of the metal powder are of size within a range of about 50 microns from the smaller to the larger particles to avoid dense packing thereof.

10. An orthodontic bracket as claimed in claim 2, wherein the said sintered layer of metal powder is carried by a separate thin metal foil constituting part of the bracket and fixed to the remainder of the bracket body.

11. An orthodontic bracket as claimed in claim 10, wherein the said metal foil is of thickness about 0.1 to 0.25 mm, and the total thickness of the metal foil and the sintered layer is about 0.15 to 0.45 mm.

12. An orthodontic bracket as claimed in claim 2, wherein the metal powder is of particle size about 30 to 50 microns.

13. An orthodontic bracket as claimed in claim 2, wherein the particles of the metal powder are of size within a range of about 50 microns from the smaller to the larger particles to avoid dense packing thereof.

14. An orthodontic bracket as claimed in claim 1, wherein the said sintered layer is applied directly by the sintering to the lingual face of the bracket body.

15. An orthodontic bracket as claimed in claim 2, wherein the said sintered layer is applied directly by the sintering to the lingual face of the bracket body.

16. An orthodontic bracket comprising an attachment base for the adhesion of said bracket to a tooth and having a tooth-engaging surface having an area of about 3×4 mm, and a porous coating on said tooth-engaging surface consisting of metal particles joined to each other and to said tooth-engaging surface at their points of contact therewith, said porous coating having a thickness of about 50 to about 200 microns and a porosity exhibiting excellent mechanical keying properties when a cement is applied thereto, said particles having a particle size of about 10 to about 150 microns, and said porous coating, the interface between said porous coating and said tooth-engaging surface, and said tooth-engaging surface having a structural strength of at least 0.5 kg/mm$^2$.

17. The bracket of claim 16, wherein said metal particles have a particle size of about 30 to about 50 microns.

18. The bracket of claim 16, wherein said metal particles have a particle size of about 10 microns.

19. The bracket of claim 16, 17 or 18 constructed of stainless steel.

20. An orthodontic bracket comprising a bracket body having a lingual surface which is applied to an acid-etched surface of a tooth on which the bracket body is to be mounted and bonded by a bonding material, the said lingual surface having thereon so as to be interposed between the said lingual and acid-etched surfaces a thin sintered layer of metal powder of thickness about 0.05 to about 0.2 mm and of particle size about 10 to about 150 microns, the sintered layer being porous to the bonding material and having pores extending from the surface thereof which receives the bonding material so as to provide a three-dimensional interconnecting network of capillaries that will become filled with the bonding material to exhibit excellent mechanical keying properties, the bracket being adhered to the tooth to an extent that a force of at least 0.5 kg/mm$^2$ is required to separate the bracket from the tooth.

21. An orthodontic bracket comprising a bracket body having a lingual surface which is applied to an acid-etched surface of a tooth upon which the bracket body is to be mounted and bonded by a bonding material, said lingual surface having thereon so as to be interposed between the said lingual surface and the said acid-etched tooth surface a thin sintered layer of metal particles having a thickness of about 0.5 to about 0.2 mm and produced from metal particles having a particle size of about 10 to about 150 microns, the sintered layer forming an integral porous layer with excellent mechanical keying properties when the bonding material is applied thereto such as to adhesion of the bracket to the tooth to the extent that the adhere the bracket to the tooth is at least 0.5 kg/mm$^2$, the sintered layer having pores extending from the surface thereof which receives bonding material so as to provide a 3-dimensional interconnecting network of capillaries which can be filled with the bonding material, the surface of the sintered layer corresponding at least approximately to the etched tooth surface to facilitate the bonding of the bracket to the tooth surface.

* * * * *